US005396561A

United States Patent [19]

Popovich et al.

[11] Patent Number: 5,396,561

[45] Date of Patent: Mar. 7, 1995

[54] ACTIVE ACOUSTIC ATTENUATION AND SPECTRAL SHAPING SYSTEM

[75] Inventors: Steven R. Popovich, Stoughton; Mark C. Allie, Oregon, both of Wis.

[73] Assignee: Nelson Industries, Inc., Stoughton, Wis.

[21] Appl. No.: 920,259

[22] Filed: Jul. 27, 1992

Related U.S. Application Data

[63] Continuation-in-part of Ser. No. 613,102, Nov. 14, 1990, Pat. No. 5,172,416.

[51] Int. Cl.[6] ........................ A61F 11/06; H03B 29/00

[52] U.S. Cl. ........................ 381/71

[58] Field of Search ........................ 381/71, 94, 56

[56] References Cited

U.S. PATENT DOCUMENTS

| | | | |
|---|---|---|---|
| 4,566,118 | 1/1986 | Chaplin et al. . | |
| 4,654,871 | 3/1987 | Chaplin et al. . | |
| 4,677,676 | 6/1987 | Eriksson . | |
| 4,677,677 | 6/1987 | Eriksson . | |
| 4,736,431 | 4/1988 | Allie et al. . | |
| 4,805,733 | 2/1989 | Kato et al. | 381/71 |
| 4,815,139 | 3/1989 | Eriksson et al. . | |
| 4,837,834 | 6/1989 | Allie . | |
| 4,953,217 | 8/1990 | Twiney et al. . | |
| 4,987,598 | 1/1991 | Eriksson . | |
| 5,022,082 | 6/1991 | Eriksson et al. . | |
| 5,033,082 | 7/1991 | Eriksson et al. . | |
| 5,105,377 | 4/1992 | Ziegler, Jr. . | |
| 5,172,416 | 12/1992 | Allie et al. | 381/71 |

OTHER PUBLICATIONS

"Noise Subtracting Filter Study", John Kaunitz and Bernard Widrow, Stanford University, Oct. 3, 1973, pp. 1–27 and 115–121.

"Active Adaptive Sound Control In A Duct: A Computer Simulation", J. C. Burgess, Journal of Acoustic Society of America, 70(3), Sep., 1981, pp. 715–726.

*Introduction To Communication Systems*, Ferrel G. Stremler, Addison–Wesley Publishing Company, 1982, pp. 314–327.

"Number Theory In Science and Communications", Berlin: Springer–Verlag, M. R. Schroeder, 1984, pp. 252–261.

"Adaptive Filters: Structures, Algorithms, and Applications", Honig et al The Kluwer International Series in Engineering and Computer Science, VLSI, Computer Architecture and Digital Signal Processing, 1984.

"Adaptive Signal Processing", Widrow and Stearns, Prentice–Hall, 1985, pp. 349–351.

*Primary Examiner*—Curtis Kuntz
*Assistant Examiner*—Ping J. Lee
*Attorney, Agent, or Firm*—Andrus, Sceales, Starke & Sawall

[57] ABSTRACT

An active acoustic system provides attenuation and spectral shaping of an acoustic wave. A phase lock loop (304) phase locks to the input acoustic wave (6) and generates (306) a desired signal or tone (308) in given phase relation therewith. An error signal (44) from an error transducer or microphone (16) is summed (302) with the desired signal (308) and the resultant sum is supplied to the error input (202) of an adaptive filter model (40) which outputs a correction signal (46) to an output transducer or speaker (14) to introduce the canceling and shaping acoustic wave. In other embodiments, various combinations sum the desired signal (308) with the error signal (44), the model output correction signal (46), and the model input signal (42). Speaker and error path compensation (146, 318, 320) and feedback compensation (340) is provided.

26 Claims, 7 Drawing Sheets

FIG. 7
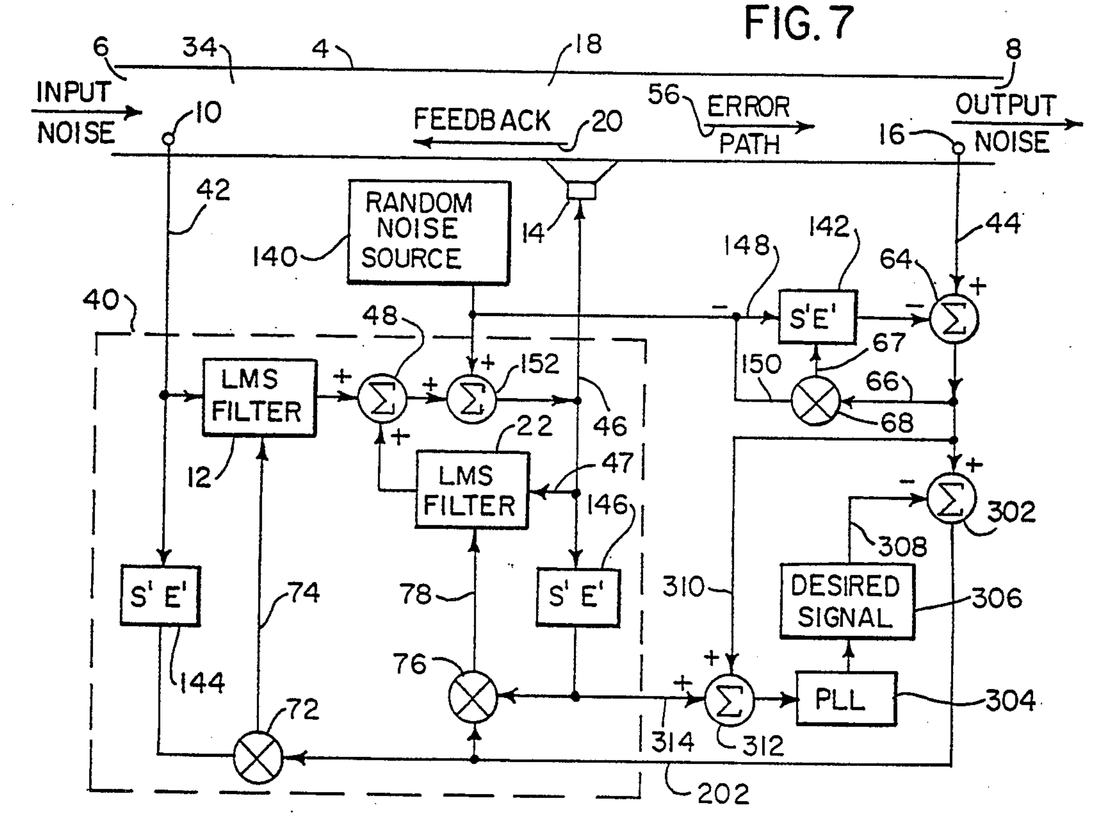
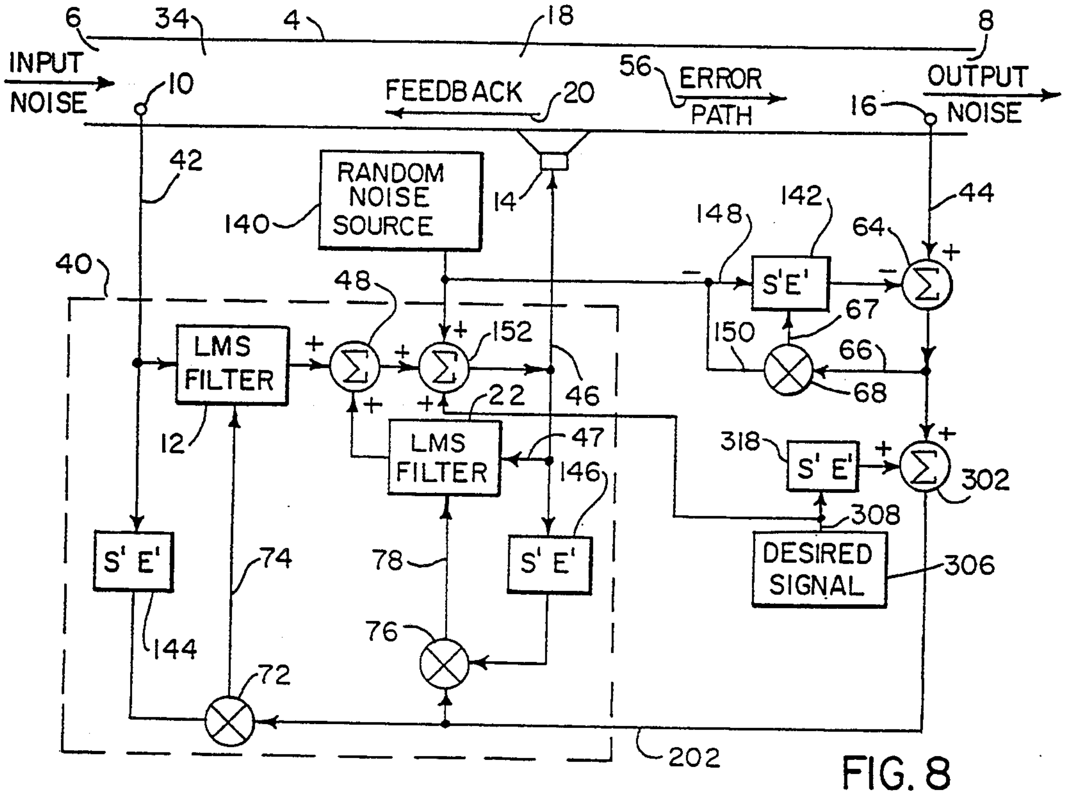
FIG. 8

FIG.9
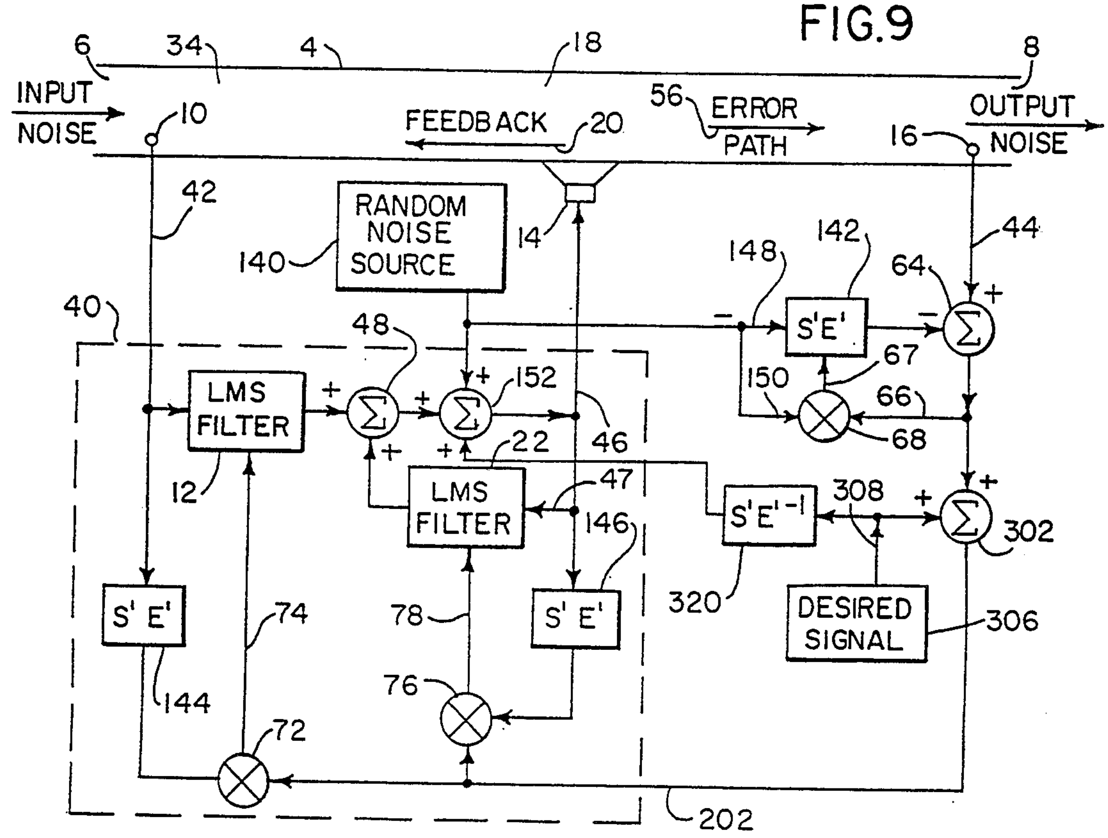
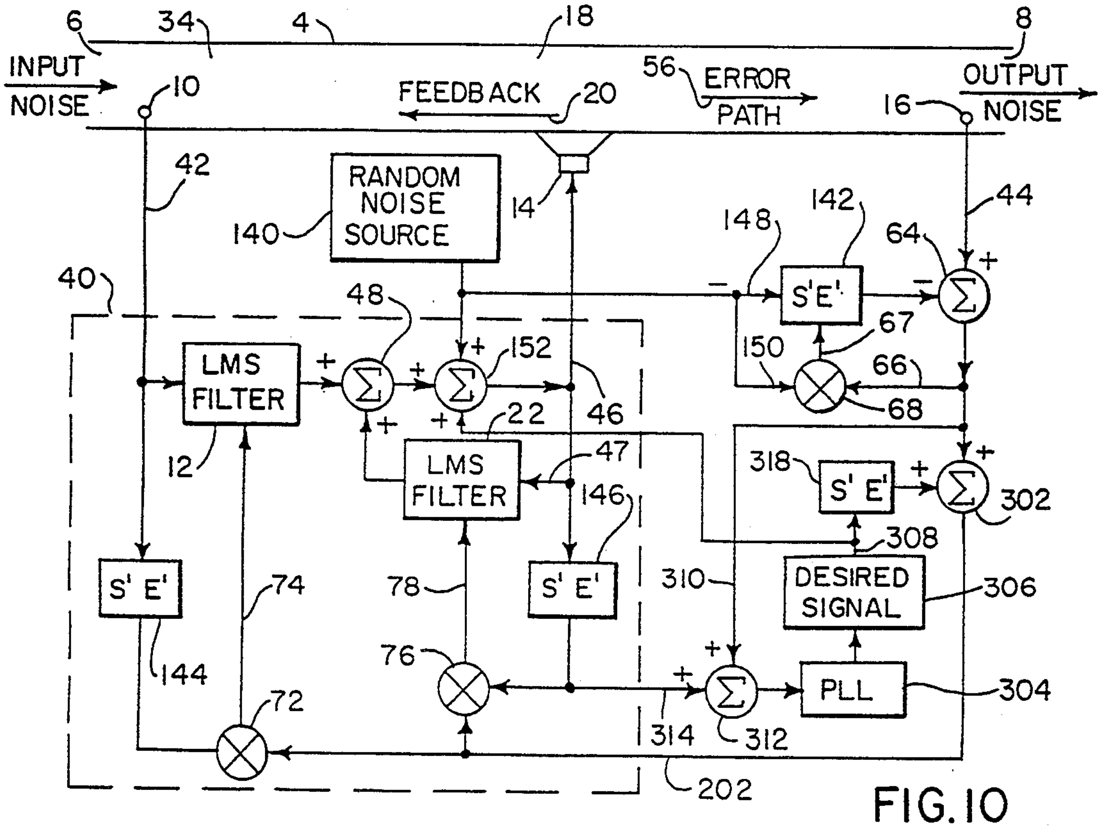
FIG.10

ACTIVE ACOUSTIC ATTENUATION AND SPECTRAL SHAPING SYSTEM

CROSS REFERENCE TO RELATED APPLICATION

This application is a continuation-in-part of application Ser. No. 07/613,102, filed Nov. 14, 1990, now U.S. Pat. No. 5,172,416, issued Dec. 15, 1992.

BACKGROUND AND SUMMARY

The invention relates to active acoustic attenuation systems, and provides a system for attenuating and spectrally shaping an acoustic wave.

The invention arose during continuing development efforts relating to the subject matter shown and described in U.S. Pat. Nos. 4,677,676, 4,677,677, 4,736,431, 4,815,139, 4,837,834, 4,987,598, 5,022,082, and 5,033,082, incorporated herein by reference.

Active attenuation involves injecting a canceling acoustic wave to destructively interfere with and cancel an input acoustic wave. In an active acoustic attenuation system, the output acoustic wave is sensed with an error transducer such as a microphone which supplies an error signal to a control model which in turn supplies a correction signal to a canceling transducer such as a loudspeaker which injects an acoustic wave to destructively interfere with and cancel the input acoustic wave. The acoustic system is modeled with an adaptive filter model.

In the invention of the noted parent application, the error signal from the error transducer, e.g. error microphone, is specified to correspondingly specify the output acoustic wave. The error signal is specified by summing the error signal with a desired signal to provide an error signal to the error input of the system model such that the model outputs the correction signal to the output transducer, e.g. speaker, to introduce the canceling acoustic wave such that the desired signal is present in the output acoustic wave. This provides a desired sound rather than complete cancellation.

The present invention provides further improvements for spectrally shaping the acoustic wave.

In one aspect of the present invention, the system includes a phase lock loop phase locked to the input acoustic wave, and generates a desired signal in given phase relation therewith. The error signal from the error transducer is summed with the desired signal from the phase lock loop, and the resultant sum is supplied to the error input of the model such that the model outputs the correction signal to the output transducer to introduce the canceling and shaping acoustic wave.

In another aspect, a first summer sums the error signal from the error transducer with a desired signal and supplies the resultant sum to the error input of the model, and a second summer sums the correction signal from the model with the desired signal and supplies the resultant sum to the output transducer.

In a further aspect, another summer sums the error signal from the error transducer with the correction signal supplied through a copy of a model of the output transducer and error path and supplies the resultant sum to the first summer.

In another aspect, the desired signal is supplied through a copy of a model of the output transducer and error path to the first summer.

In a further aspect, the desired signal is supplied through an inverse of a copy of a model of the output transducer and error path to the second summer.

In another aspect, a first summer sums the error signal from the error transducer with a desired signal and supplies the resultant sum to the error input of the model, and a second summer sums the input signal to the model with the desired signal and supplies the resultant sum to the model input.

BRIEF DESCRIPTION OF THE DRAWINGS

FIG. 7 is a schematic illustration of an active acoustic attenuation system in accordance with the present invention.

FIG. 8 is like FIG. 7 and shows a further embodiment.

FIG. 9 is like FIG. 7 and shows a further embodiment.

FIG. 10 is like FIG. 7 and shows a further embodiment.

DETAILED DESCRIPTION

Figure 1:
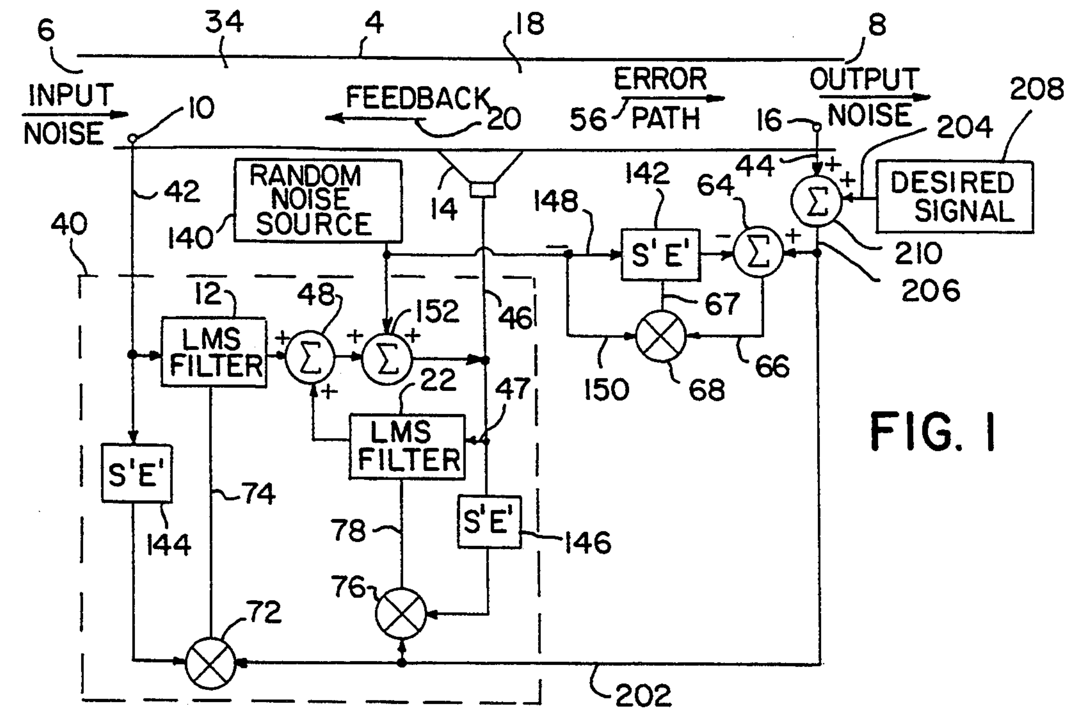
FIG. 1 is a schematic illustration of an active acoustic attenuation system in the noted parent application.

FIG. 1 shows an active acoustic attenuation system like that shown in FIG. 19 of incorporated U.S. Pat. No. 4,677,676 and uses like reference numerals from FIGS. 19 and 20 of the '676 patent where appropriate to facilitate understanding.

The acoustic system in FIG. 1 has an input 6 for receiving an input acoustic wave and an output 8 for radiating an output acoustic wave. The active acoustic attenuation method and apparatus introduces a canceling acoustic wave from an output transducer, such as speaker 14. The input acoustic wave is sensed with an input transducer, such as microphone 10. The output acoustic wave is sensed with an error transducer, such as microphone 16, providing an error signal 44. The acoustic system is modeled with an adaptive filter model 40 having a model input 42 from input transducer 10 and an error input 202 from error signal 44 and outputting a correction signal 46 to output transducer 14 to introduce the canceling acoustic wave. In the system in FIG. 1, error signal 44 is modified to correspondingly shape the attenuation of the output acoustic wave.

In one embodiment, error signal 44 is specified by summing the error signal with a desired tone signal 204 to provide a specified error signal 206 to error input 202 such that model 40 outputs correction signal 46 to output transducer 14 to introduce the canceling acoustic wave such that a desired tone is present in the output acoustic wave. The tone signal is generated by tone generator 208, provided by a Hewlett Packard 35660 spectrum analyzer. Summer 210 is provided at the output of error transducer 16 and sums the desired tone signal 204 with error signal 44 and provides the result 206 to the error input 202 of model 40. This specifies the error signal to correspondingly specify the output acoustic wave.

Without tone generator 208 and summer 210, the system operates as described in the incorporated '676 patent and cancels the input acoustic wave such that error signal 44 is zero. With tone generator 208 and summer 210, the tone signal 204 is added or injected into error signal 44, such that model 40 sees a non-zero error signal at error input 202 and in turn acts to inject an acoustic wave at speaker 14 to reduce the error input at 202 to zero. This is accomplished by canceling all of the input acoustic wave except for a tone which is 180° out of phase with tone signal 204. Hence, error microphone 16 senses such remaining tone, which tone appears in error signal 44 and is summed with and 180° out of phase with tone signal 204, thus resulting in a zero error signal 206 which is supplied to the error input 202 of model 40.

In one embodiment, error signal 44 and tone signal 204 are additively summed at summer 206, as shown in FIG. 1. In this embodiment, the tone in the output acoustic wave sensed by microphone 16 will be 180° out of phase with tone signal 204. In another embodiment, error signal 44 and tone signal 204 are subtractively summed at summer 210, in which case the tone in the output acoustic wave sensed by microphone 16 will be in phase with tone signal 204.

Figure 2:
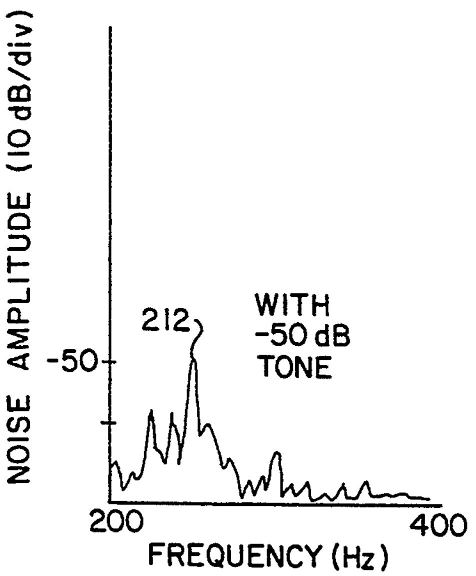
FIGS. 2–5 are graphs illustrating operation of the system of FIG. 1.
Figure 3:
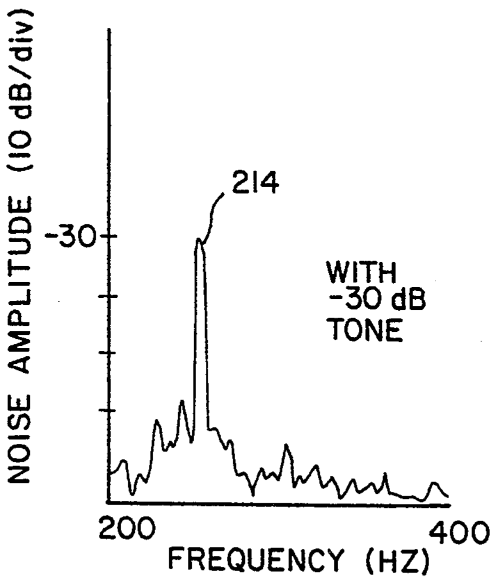
Figure 4:
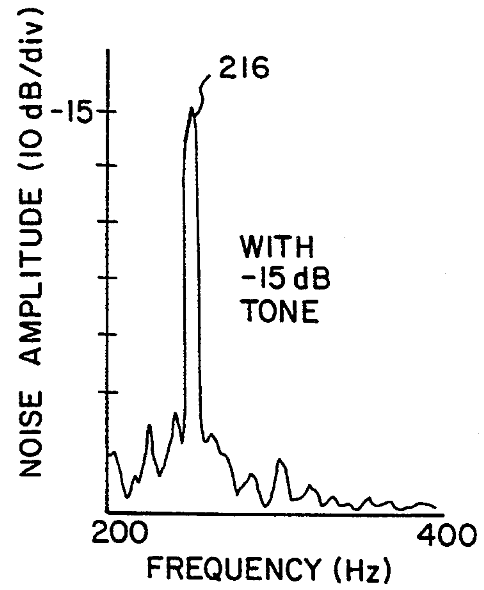
Figure 5:
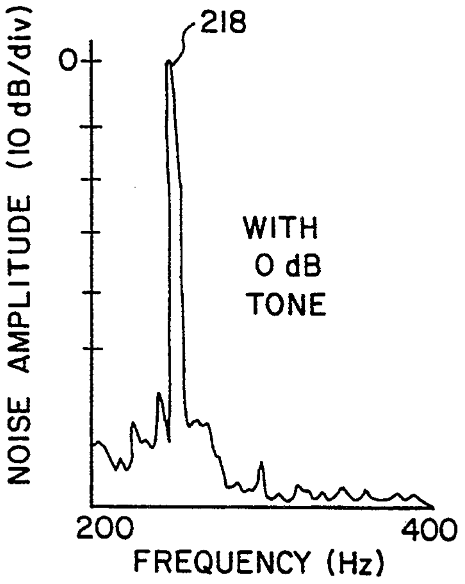

FIGS. 2–5 show shaping of the spectrum of the output acoustic wave provided by the system of FIG. 1 when fully adapted and canceling an undesired input acoustic wave. FIGS. 2–5 are graphs showing frequencies in Hertz on the horizontal axis, and noise amplitude in decibels on the vertical axis, and with increasing amplitudes of injected tones 204 from −50 dB relative to the uncancelled output acoustic wave in FIG. 2, to −30 dB in FIG. 3, to −15 dB in FIG. 4, to 0 dB in FIG. 5. As shown, a small amplitude tone 212, FIG. 2, is present in the output acoustic wave when a small amplitude −50 dB tone 204 is injected. When the amplitude of the injected tone 204 is increased to −30 dB, FIG. 3, the amplitude of the tone in the output acoustic wave also increases, as shown at 214, and continues to increase as shown at 216 and 218, FIGS. 4 and 5, respectively, when the injected tone amplitude is increased to −15 dB and then to 0 dB, respectively. Thus, the tonal content of the output acoustic wave at 8 may be specified through the addition of tone 204. The system is not limited to a single tone as shown in FIGS. 2–5, but signal generator 208 may be used to create a series of tones.

The system of FIG. 1 is further particularly useful in combination with the system in the above noted '676 patent and provides an active attenuation system and method for attenuating an undesirable output acoustic wave by introducing a canceling acoustic wave from an output transducer such as speaker 14, and for adaptively compensating for feedback along feedback path 20 to input 6 from speaker or transducer 14 for both broad band and narrow band acoustic waves, on-line without off-line pre-training, and providing adaptive modeling and compensation of error path 56 and adaptive modeling and compensation of speaker or transducer 14, all on-line without off-line pre-training.

Input transducer or microphone 10 senses the input acoustic wave at 6. The combined output acoustic wave and canceling acoustic wave from speaker 14 are sensed with an error microphone or transducer 16 spaced from speaker 14 along error path 56 and providing an error signal at 44. The acoustic system or plant P, FIG. 20 of the '676 patent, is modeled with adaptive filter model 40 provided by filters 12 and 22 and having a model input at 42 from input microphone 10 and an error input at 44 from error microphone 16. Model 40 outputs a correction signal at 46 to speaker 14 to introduce canceling sound such that the error signal at 44 approaches a given value, such as zero. Feedback path 20 from speaker 14 to input microphone 10 is modeled with the same model 40 by modeling feedback path 20 as part of the model 40 such that the latter adaptively models both the acoustic system P and the feedback path F, without separate modeling of the acoustic system and feedback path, and without a separate model pre-trained off-line solely to the feedback path with broad band noise and fixed thereto.

An auxiliary noise source 140 introduces noise into the output of model 40. The auxiliary noise source is random and uncorrelated to the input noise at 6, and in preferred form is provided by a Galois sequence, M. R. Schroeder, Number Theory in Science and Communications, Berlin: Springer-Verlag, 1984, pp. 252–261, though other random uncorrelated noise sources may of course be used. The Galois sequence is a pseudorandom sequence that repeats after $2^M-1$ points, where M is the number of stages in a shift register. The Galois sequence is preferred because it is easy to calculate and can easily have a period much longer than the response time of the system.

Model 142 models both the error path E 56 and the speaker output transducer S 14 on-line. Model 142 is a second adaptive filter model provided by a LMS filter. A copy S'E' of the model is provided at 144 and 146 in model 40 to compensate for speaker S 14 and error path E 56.

Second adaptive filter model 142 has a model input 148 from auxiliary noise source 140. The error signal output 44 of error path 56 at output microphone 16 is summed at summer 64 with the output of model 142 and the result is used as an error input at 66 to model 142. The sum at 66 is multiplied at multiplier 68 with the auxiliary noise at 150 from auxiliary noise source 140, and the result is used as a weight update signal at 67 to model 142.

The outputs of the auxiliary noise source 140 and model 40 are summed at 152 and the result is used as the correction signal at 46 to input speaker 14. Adaptive filter model 40, as noted above, is provided by first and second algorithm filters 12 and 22 each having an error input at 44 from error microphone 16. The outputs of first and second algorithm filters 12 and 22 are summed at summer 48 and the resulting sum is summed at summer 152 with the auxiliary noise from auxiliary noise source 140 and the resulting sum is used as the correction signal at 46 to speaker 14. An input at 42 to algorithm filter 12 is provided from input microphone 10. Input 42 also provides an input to model copy 144 of adaptive speaker S and error path E model. The output of copy 144 is multiplied at multiplier 72 with the error signal at 44 and the result is provided as weight update signal 74 to algorithm filter 12. The correction signal at 46 provides an input 47 to algorithm filter 22 and also provides an input to model copy 146 of adaptive speaker S and error path E model. The output of copy 146 and the error signal at 44 are multiplied at multiplier 76 and the result is provided as weight update signal 78 to algorithm filter 22.

Auxiliary noise source 140 is an uncorrelated low amplitude noise source for modeling speaker S 14 and error path E 56. This noise source is in addition to the input noise source at 6 and is uncorrelated thereto, to enable the S'E' model to ignore signals from the main model 40 and from plant P. Low amplitude is desired so as to minimally affect final residual acoustical noise radiated by the system. The second or auxiliary noise from source 140 is the only input to the S'E' model 142, and thus ensures that the S'E' model will correctly characterize SE. The S'E' model is a direct model of SE, and this ensures that the RLMS model 40 output and the plant P output will not affect the final converged model S'E' weights. A delayed adaptive inverse model would not have this feature. The RLMS model 40 output and plant P output would pass into the SE model and would affect the weights.

The system needs only two microphones. The auxiliary noise signal from source 140 is summed at junction 152 after summer 48 to ensure the presence of noise in the acoustic feedback path and in the recursive loop. The system does not require any phase compensation filter for the error signal because there is no inverse modeling. The amplitude of noise source 140 may be reduced proportionate to the magnitude of error signal 66, and the convergence factor for error signal 44 may be reduced according to the magnitude of error signal 44, for enhanced long term stability, "Adaptive Filters: Structures, Algorithms, And Applications" Michael L. Honig and David G. Messerschmitt, The Kluwer International Series in Engineering and Computer Science, VLSI, Computer Architecture And Digital Signal Processing, 1984.

A particularly desirable feature of the invention is that it requires no calibration, no pre-training, no presetting of weights, and no start-up procedure. One merely turns on the system, and the system automatically compensates and attenuates undesirable output noise.

Signal 204 is correlated with the input acoustic wave, preferably by correlating tone generator 208 to the input acoustic wave or by deriving signal 204 from the input acoustic wave or from a synchronizing signal correlated with the input acoustic wave, for example based on rpm. In other applications, the input microphone is eliminated and replaced by a synchronizing source for the main model 40 such as an engine tachometer. In other applications, directional speakers and/or microphones are used and there is no feedback path modeling. In other applications, a high grade or near ideal speaker is used and the speaker transfer function is unity, whereby model 142 models only the error path. In other applications, the error path transfer function is unity, e.g., by shrinking the error path distance to zero or placing the error microphone 16 immediately adjacent speaker 14, whereby model 142 models only the canceling speaker 14. The invention can also be used for acoustic waves in other fluids (e.g. water, etc.), acoustic waves in three dimensional systems (e.g. room interiors, etc.), and acoustic waves in solids (e.g. vibrations in beams, etc.).

Figure 6:
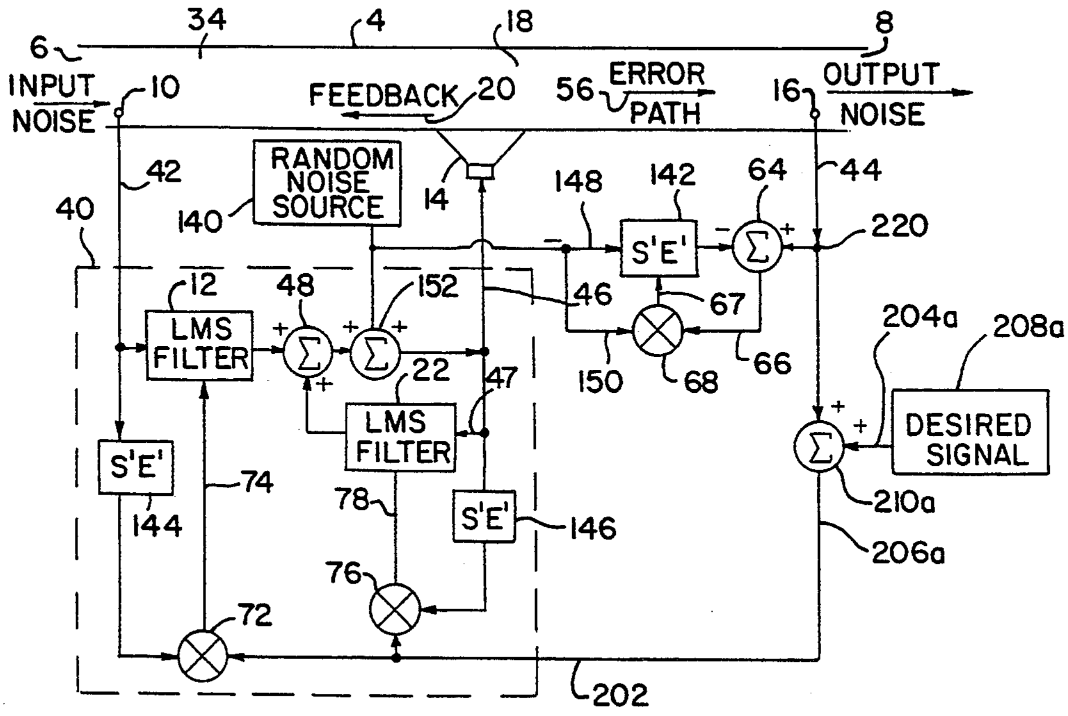
FIG. 6 is like FIG. 1 and shows an alternate embodiment.

FIG. 6 shows an alternate embodiment, and uses like reference numerals from FIG. 1 where appropriate to facilitate understanding. In FIG. 6, error signal 44 is supplied to summer 64 at node 220 before being summed at summer 210*a* with a desired tone signal 204*a* comparable to signal 204. The summing at summer 210*a* specifies the error signal to correspondingly specify the output acoustic wave, as in FIG. 1 at summer 210. Summer 210*a* is provided at the output of error transducer 16 and downstream of node 220 and sums the desired tone signal 204*a* with error signal 44 and provides the resultant specified error signal 206*a* to the error input 202 of model 40 such that model 40 outputs correction signal 46 to output transducer 14 to introduce the canceling acoustic wave such that a desired tone is present in the output acoustic wave. The tone signal is generated by tone generator 208*a*, provided by a Hewlett Packard 35660 spectrum analyzer. The embodiment in FIG. 6 prevents introduction of tone signal 204*a* into summer 64 and the error signal at 66 and model 142.

FIG. 7 uses like reference numerals from FIG. 1 where appropriate to facilitate understanding. FIG. 7 shows an active acoustic attenuation and spectral shaping system for attenuating and spectrally shaping the input acoustic wave. The output transducer provided by speaker 14 introduces a canceling and shaping acoustic wave to attenuate and shape the input acoustic wave and yield an attenuated and spectrally shaped output acoustic wave at output 8. The error transducer provided by error microphone 16 senses the output acoustic wave and provides an error signal 44. Adaptive filter model 40 models the acoustic system and has an error input 202 and outputs a correction signal 46 to output transducer 14 to introduce the canceling and shaping acoustic wave. The error signal 44 is provided through summer 64 and summer 302 to error input 202 of the model. A phase lock loop 304, for example as shown in *Introduction To Communication Systems*, Ferrel G. Stremler, Addison-Wesley Publishing Company, 1982, pages 314–327, is phase locked to the input acoustic wave and generates at tone generator 306, such as provided above by a Hewlett Packard 35660 spectrum analyzer, a desired signal or tone 308 in given phase relation with the input acoustic wave. Summer 302 sums the error signal 44 from error transducer 16 and the desired signal 308 from signal generator 306 and phase lock loop 304 and supplies the resultant sum to error input 202 of model 40. Phase lock loop 304 phase locks to the input acoustic wave by phase locking to the output acoustic wave at 8 by phase locking to error signal 44 to generate desired signal 308 in given phase relation with error signal 44.

Error signal 44 is input at line 310 and summer 312 to phase lock loop 304. The effects of the correction signal and the speaker and error path in the output acoustic wave are compensated at summer 312 by input 314 which is the correction signal 46 supplied through S'E' copy 146 which is a copy of adaptive filter model 142 which models output transducer 14 and error path 56 between output transducer 14 and error transducer 16, as described above and in incorporated U.S. Pat. No. 4,677,676. Alternatively, the input to phase lock loop 304 may be provided directly from the input acoustic wave.

As above, model 40 outputs correction signal 46 to output transducer 14 such that the noted desired signal is present in the output acoustic wave and in the error signal 44 from error transducer 16 to summer 302 such that the desired signal from error transducer 16 is canceled at summer 302 by desired signal 308 from signal generator 306 and phase lock loop 304 and such that the desired signal is absent from error input 202 to model 40. Without phase lock loop 304, signal generator 306 and summer 302, the system operates as described in the incorporated '676 patent and cancels the input acoustic wave such that error signal 44 is zero. With phase lock loop 304, signal generator 306 and summer 302, the desired signal 308 is subtractively summed with error signal 44, such that model 40 sees a non-zero error signal at error input 202 and in turn acts to inject an acoustic wave at output transducer 14 to reduce the error input at 202 to zero. This is accomplished by canceling all of the input acoustic wave except for the desired tone. Error microphone 16 senses such remaining desired tone, which tone appears in error signal 44 and is subtractively summed with signal 308 such that the resultant sum is zero, thus resulting in a zero error signal at error input 202 to model 40.

In another embodiment, error signal 44 and tone signal 308 are additively summed at summer 302, in which case model 40 cancels all of the input acoustic wave except for a tone which is 180° out of phase with tone signal 308, and error transducer 16 senses such remaining tone, which tone appears in error signal 44 and is additively summed with and 180° out of phase with tone signal 308, thus resulting in a zero error signal resultant sum at error input 202 of model 40.

If the desired signal or tone is not already present in the input acoustic wave, then model 40 generates such tone signal which is then injected at output transducer 14 and sensed by error transducer 16 and summed at summer 302 with signal 308 thus resulting in a zero resultant sum at error input 202 of model 40. In this latter embodiment, the desired signal is present in correction signal 46. In the first noted embodiments, the desired signal is absent from correction signal 46. In each of the noted embodiments, model 40 outputs correction signal 46 to output transducer 14 such that the desired signal is present in the output acoustic wave and in the error signal 44 from error transducer 16 to summer 302 such that the desired signal from error transducer 16 is canceled at summer 302 by desired signal 308 from signal generator 306 and phase lock loop 304 and such that the desired signal is absent from error input 202 to model 40.

FIG. 8 shows a further embodiment, and uses like reference numerals from FIG. 7 where appropriate to facilitate understanding. Summer 152 sums desired signal 308 from signal generator 306 with the correction signal from the model and outputs the resultant sum to output transducer 14 such that the desired signal is present in the output acoustic wave and in error signal 44 from error transducer 16 to summer 302. The desired signal from error transducer 16 is canceled at summer 302 by desired signal 308 from signal generator 306, such that the desired signal is absent from error input 202 to model 40. The desired signal 308 is added and injected at summer 152 and output transducer 14 into the acoustic wave, and is subtracted or canceled at summer 302. In this embodiment, the signal desired in the output acoustic wave at output 8 need not be already present in the input acoustic wave at input 6, nor must model 40 generate such tone. The embodiment in FIG. 8 is preferred where the desired output tone is not present in the input acoustic wave and it is preferred that model 40 be devoted to cancellation convergence without also having to generate a desired tone.

Auxiliary noise source 140 introduces noise into the model, as described above and in the incorporated '676 patent. Error transducer 16 also senses the auxiliary noise from the auxiliary noise source. Adaptive filter model 142 has a model input 148 from auxiliary noise source 140 and models the output transducer or speaker, S, 14, and the error path, E, 56, between output transducer 14 and error transducer 16. In addition to model copies S'E' 144 and 146, another copy S'E' of adaptive filter model 142 is provided at 318 to compensate for speaker, S, 14, and error path, E, 56. Model copy 318 has an input from desired signal generator 306, and an output to summer 302.

FIG. 9 shows a further embodiment, and uses like reference numerals from FIG. 8 where appropriate to facilitate understanding. In FIG. 9, the model copy 318 of FIG. 8 is eliminated, and instead an inverse copy 320 of adaptive filter model 142 is provided, and has an input from desired signal 308 and an output to summer 152. This compensates for the speaker error path 14, 56.

FIG. 10 shows a further embodiment, and uses like reference numerals from FIGS. 7 and 8 where appropriate to facilitate understanding. In the embodiment in FIG. 10, the phase lock loop 304 of FIG. 7 is used in combination with the embodiment of FIG. 8. In FIG. 10, model copy 318 may be replaced by inverse copy 320 as in FIG. 9.

Figure 11:
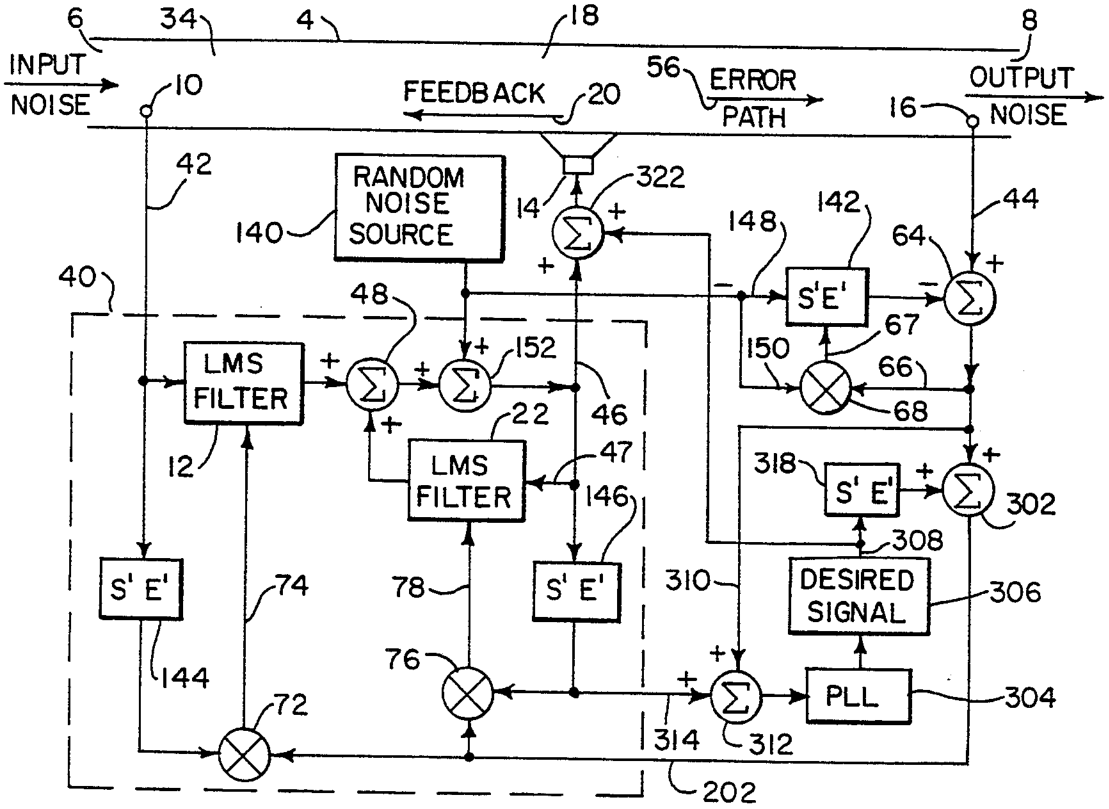
FIG. 11 is like FIG. 7 and shows a further embodiment.

FIG. 11 shows a further embodiment, and uses like reference numerals from FIGS. 7 and 8 where appropriate to facilitate understanding. FIG. 11 shows another alternate embodiment to FIG. 8 wherein desired signal 308 is supplied to summer 322, rather than summer 152. Either of summers 322 or 152 may be used to sum the model output correction signal with the desired signal, though it is preferred to use summer 152 such that the resultant sum is supplied in the model loop to input 47 of filter 22.

Figure 12:
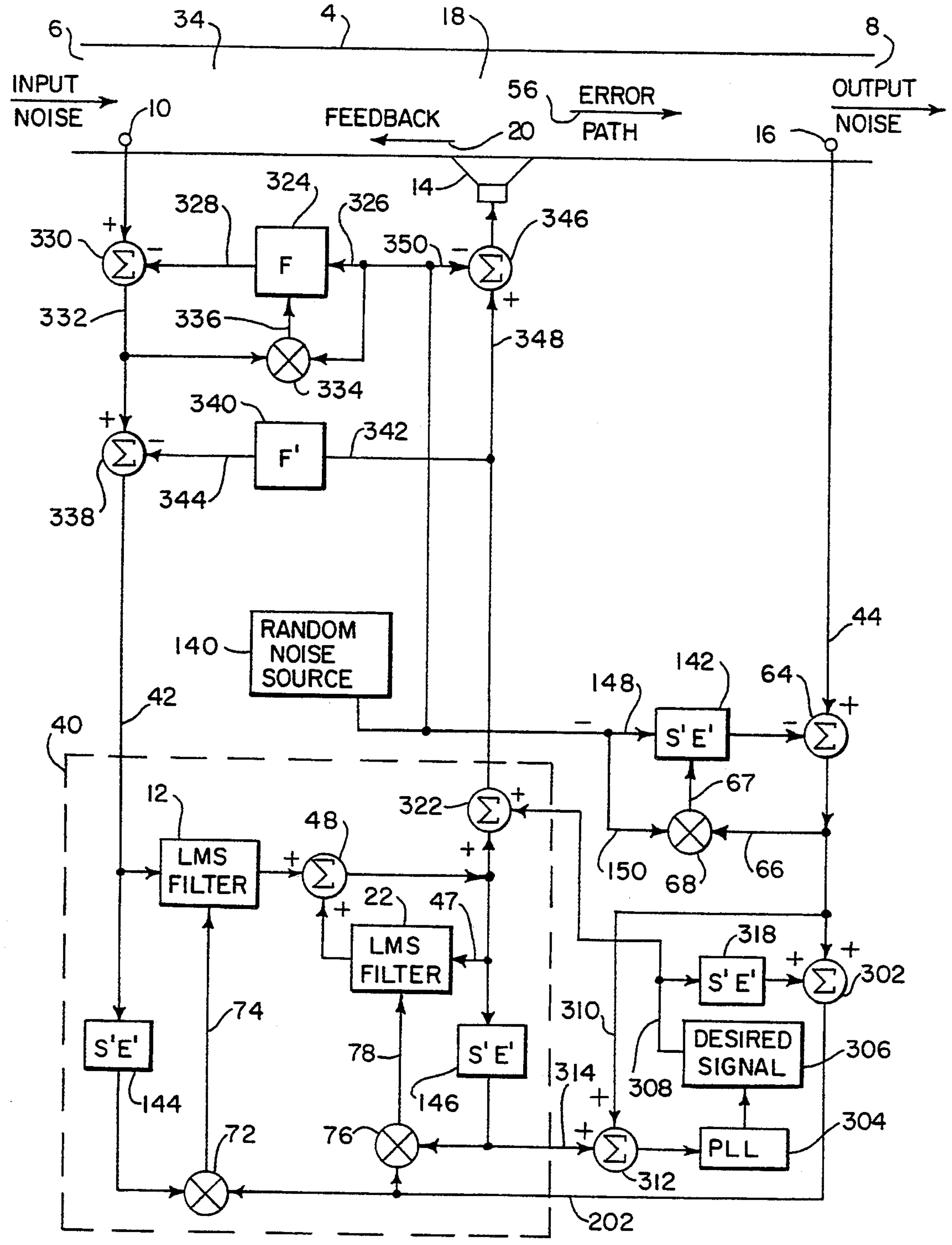
FIG. 12 is like FIG. 7 and shows a further embodiment.

FIG. 12 shows a further embodiment, and uses like reference numerals from FIG. 11 where appropriate to facilitate understanding. In FIG. 12, an adaptive filter model F at 324 models the feedback path 20 from output transducer 14 to input transducer 10. Model 324 has a model input 326 from auxiliary noise source 140, and a model output 328 summed at summer 330 with the input signal from input transducer 10. The output resultant sum 332 from summer 330 provides the error signal for model 324 and is multiplied at multiplier 334 with model input 326 and the result is provided as a weight update signal 336 to model 324. Resultant sum 332 is also provided through summer 338 to the model input of adaptive filter model 40. A copy F' 340 of adaptive filter model 324 has an input 342 from the output of summer 322, and has an output 344. Summer 338 sums the output 344 of model copy 340 and the output 332 of summer 330 and supplies the resultant sum to model input 42 of adaptive filter model 40. A further summer 346 has a first input 348 from the output of summer 322, and has a second input 350 from auxiliary noise source 140, and supplies the resultant sum to output transducer 14.

Figure 13:
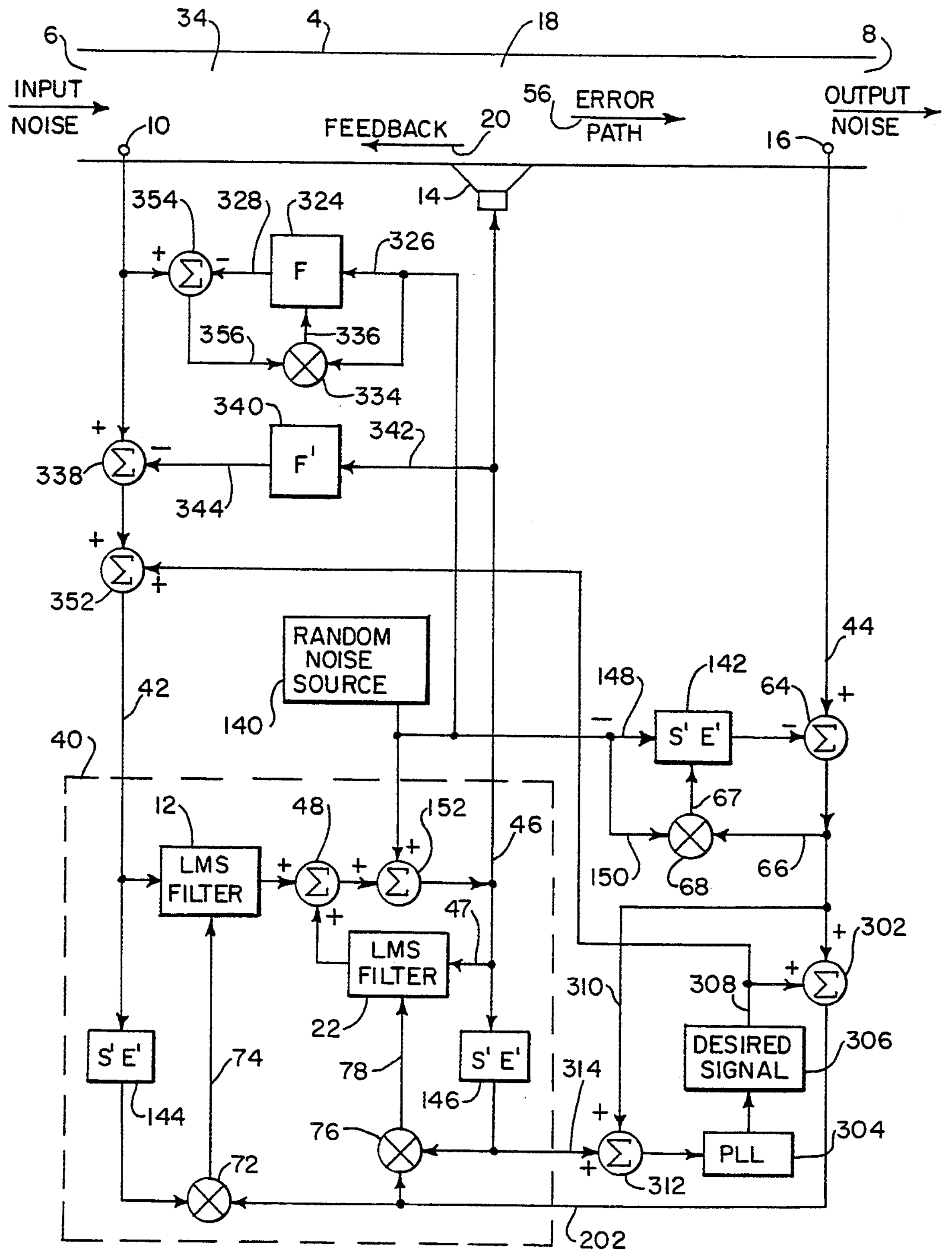
FIG. 13 is like FIG. 7 and shows a further embodiment.

FIG. 13 shows a further embodiment, and uses like reference numerals from FIG. 12 where appropriate to facilitate understanding. In FIG. 13, summer 352 sums desired signal 308 from signal generator 306 and the input signal from input transducer 10 through summer 338, and supplies the resultant sum to model input 42 of adaptive filter model 40. Adaptive filter model F 324 models feedback path 20 and has a model input at 326, a model output 328 summed with the signal from input transducer 10 at summer 354 whose output resultant sum 356 provides the error signal multiplied at multiplier 334 to provide the weight update signal 336. The input signal from input transducer 10 is provided directly to summer 338 in FIG. 13, unlike FIG. 12. Summers 322 and 346 of FIG. 12 are eliminated in FIG. 13.

In further embodiments, the input microphone or transducer 10 is eliminated, and the input signal is provided by a transducer such as a tachometer which provides the frequency of a periodic input acoustic wave such as from an engine or the like. Further alternatively, the input signal may be provided by one or more error signals, in the case of a periodic noise source, "Active Adaptive Sound Control In A Duct: A Computer Simulation", J. C. Burgess, Journal of Acoustic Society of America, 70(3), September 1981, pp. 715–726. In other applications, directional speakers and/or microphones are used and there is no feedback path modeling. In other applications, a high grade or near ideal speaker is used and the speaker transfer function is unity, whereby model 142 models only the error path. In other applications, the error path transfer function is unity, e.g. by shrinking the error path distance to zero or placing the error microphone 16 immediately adjacent speaker 14, whereby model 142 models only the canceling speaker 14. The invention can also be used for acoustic waves in other fluids, e.g. water, etc., acoustic waves in three dimensional systems, e.g. room interiors, etc., and acoustic waves in solids, e.g. vibrations in beams, etc. The system includes a propagation path or environment such as within or defined by a duct or plant 4, though the environment is not limited thereto and may be a room, a vehicle cab, free space, etc. The system has other applications such as vibration control in structures or machines, wherein the input and error transducers are accelerometers for sensing the respective acoustic waves, and the output transducers are shakers for outputting canceling acoustic waves. An exemplary application is active engine mounts in an automobile or truck for damping engine vibration. The system is also applicable to complex structures for vibration control. In general, the system may be used for attenuation and spectral shaping of an undesired elastic wave in an elastic medium, i.e. an acoustic wave propagating in an acoustic medium.

It is recognized that various equivalents, alternatives and modifications are possible within the scope of the appended claims.

We claim:

1. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, an adaptive filter model modeling said acoustic system and having an error input and outputting a correction signal to said output transducer to introduce the canceling and shaping acoustic wave, a phase lock loop phase locked to said input acoustic wave and generating a desired signal in given phase relation with said input acoustic wave, a summer summing the error signal from said error transducer and the desired signal from said phase lock loop and supplying the resultant sum to said error input of said model such that said model outputs said correction signal to said output transducer to introduce the canceling and shaping acoustic wave, wherein said model outputs said correction signal to said output transducer such that said desired signal is present in said output acoustic wave and in the error signal from said error transducer to said summer such that the desired signal from said error transducer is canceled at said summer by the desired signal from said phase lock loop and such that said desired signal is absent from said error input to said model, and wherein said desired signal is present in said correction signal.

2. The system according to claim 1 wherein said phase lock loop has an input from said error signal, and phase locks to said input acoustic wave by phase locking to said output acoustic wave by phase locking to said error signal to generate said desired signal in given phase relation with said input signal.

3. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, an adaptive filter model modeling said acoustic system and having an error input and outputting a correction signal to said output transducer to introduce the canceling and shaping acoustic wave, a phase lock loop phase locked to said input acoustic wave and generating a desired signal in given phase relation With said input acoustic wave, a first summer summing the error signal from said error transducer and the desired signal from said phase lock loop and supplying the resultant sum to said error input of said model such that said model outputs said correction signal to said output transducer to introduce the canceling and shaping acoustic wave, a second summer summing said desired signal from said phase lock loop with said correction signal from said model and outputting the resultant sum to said output transducer such that said desired signal is present in said output acoustic wave and in the error signal from said error transducer to said first summer and such that said desired signal from said error transducer is canceled at said first summer by said desired signal from said phase lock loop and such that said desired signal is absent from said error input to said model from said first summer.

4. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, an adaptive filter model modeling said acoustic system and having an error input and outputting a correction signal to said output transducer to introduce the canceling and shaping acoustic wave, a phase lock loop phase locked to said input acoustic wave and generating a desired signal in given phase relation with said input acoustic wave, a summer summing the error signal from said error transducer and the desired signal from said phase lock loop and supplying the resultant sum to said error input of said model such that said model outputs said correction signal to said output transducer to introduce the canceling and shaping acoustic wave, an auxiliary noise source introducing auxiliary noise such that said error transducer also senses the auxiliary noise from said auxiliary noise source, a second adaptive filter model having a model input from said auxiliary noise source and modeling said output transducer and the error path between said output transducer and said error transducer, and a copy of said second adaptive filter model having an input from said phase lock loop and having an output to said summer, such that the desired signal is supplied through said copy to the summer.

5. The system according to claim 4 comprising a second copy of said second adaptive filter model having an input from said correction signal and having an output, a second summer having a first input from the error signal from said error transducer and a second input from the output of said second copy of said second adaptive filter model, said second summer having an output to said phase lock loop.

6. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, an adaptive filter model modeling said acoustic system and having an error input and outputting a correction signal to said output transducer to introduce the canceling and shaping acoustic wave, a phase lock loop phase locked to said input acoustic wave and generating a desired signal in given phase relation with said input acoustic wave, a first summer summing the error signal from said error transducer and the desired signal from said phase lock loop add supplying the resultant sum to said error input of said model such that said model outputs said correction signal to said output transducer to introduce the canceling and shaping acoustic wave, a second summer summing said desired signal from said phase lock loop with said correction signal from said model and outputting the resultant sum to said output transducer such that said desired signal is present in said output acoustic wave and in the error signal from said error transducer to said first summer and such that said desired signal from said error transducer is canceled at said first summer by said desired signal from said phase lock loop and such that said desired signal is absent from said error input to said model from said first mentioned summer, an auxiliary noise source introducing auxiliary noise such that said error transducer also senses the auxiliary noise from said auxiliary noise source, a second adaptive filter model having a model input from said auxiliary noise source and modeling said output transducer and the error path between said output transducer and said error transducer, and a copy of said second adaptive filter model having an input from said phase lock loop and having an output to said first summer, such that the desired signal is supplied through said copy to the first summer, a second copy of said second adaptive filter model having an input from said correction signal and having an output, a third summer having a first input from the error signal from said error transducer and a second input from the output of said second copy of said second adaptive filter model, said third summer having an output to said phase lock loop.

7. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, an adaptive filter model modeling said acoustic system and having an error input and outputting a correction signal to said output transducer to introduce the canceling and shaping acoustic wave, a phase lock loop phase locked to said input acoustic wave and generating a desired signal in given phase relation with said input acoustic wave, a summer summing the error signal from said error transducer and the desired signal from said phase lock loop and supplying the resultant sum to said error input of said model such that said model outputs said correction signal to said output transducer to introduce the canceling and shaping acoustic wave, an auxiliary noise source introducing auxiliary noise such that said error transducer also senses the auxiliary noise from said auxiliary noise source, a second adaptive filter model having a model input from said auxiliary noise source and modeling said output transducer and the error path between said output transducer and said error transducer, a first copy of said second adaptive filter model having an input from said phase lock loop and having an output adding with the error signal at the summer, such that the desired signal is supplied through said first copy to the summer, a second copy of said second adaptive filter model having an input from said correction signal and having an output, a second summer summing said correction signal and the desired signal from said phase lock loop and supplying the resultant sum to said output transducer, a third summer summing the error signal from said error transducer and the output of said second copy of said second adaptive filter model and supplying the resultant sum to said phase lock loop for generating said desired signal.

8. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, an adaptive filter model modeling said acoustic system and having an error input and outputting a correction signal to said output transducer to introduce the canceling and shaping acoustic wave, a phase lock loop phase locked to said input acoustic wave and generating a desired signal in given phase relation with said input acoustic wave, a summer summing the error signal from said error transducer and the desired signal from said phase lock loop and supplying the resultant sum to said error input of said model such that Said model outputs said correction signal to said output transducer to introduce the canceling and shaping acoustic wave, a signal generator having an input from said phase lock loop and an output providing said desired signal.

9. The system according to claim 1 wherein said model outputs said correction signal to said output transducer such that said desired signal is present in said output acoustic wave and in the error signal from said error transducer to said summer such that the desired signal from said error transducer is canceled at said summer by the desired signal from said phase lock loop and such that said desired signal is absent from said error input to said model.

10. The system according to claim 9 wherein said desired signal is absent from said correction signal.

11. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, an adaptive filter model modeling said acoustic system and having an error input and outputting a correction signal, a first summer summing the error signal from said error transducer and a desired signal and supplying the resultant sum to said error input of said model, a second summer summing said correction signal from said model and said desired signal and outputting the resultant sum to said output transducer.

12. The system according to claim 11 comprising a second model modeling said output transducer and the error path between said output transducer and said error transducer, and a first copy of said second model having an input from said desired signal and an output to said first summer such that said desired signal is supplied through said firs copy to said first summer.

13. The system according to claim 12 comprising a second copy of said second model having an input from said correction signal and having an output, a third summer summing the error signal from said error transducer and said output of said second copy of said second model and supplying the resultant sum to said first copy of said second model as the desired signal.

14. The system according to claim 13 wherein said resultant sum from said third summer is supplied through a signal generator to said first copy of said second model.

15. The system according to claim 11 comprising a second model modeling said output transducer and the error path between said output transducer and said error transducer, and an inverse copy of said second model having an input from said desired signal and an output to said second summer.

16. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, a first adaptive filter model modeling said acoustic system and having an error input and outputting a correction signal to said output transducer to introduce the canceling and shaping acoustic wave, a second model modeling said output transducer and the error path between said output transducer and said error transducer, a copy of said second model having an input from said correction signal and having an output, a first summer summing the error signal from said error transducer and said output of said copy of said second model, a second summer summing the error signal from said error transducer and the output of said first summer and supplying the resultant sum to said error input of said first model.

17. The system according to claim 16 wherein said output of said first summer is supplied through a signal generator to said second summer.

18. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, a first adaptive filter model modeling said acoustic system and having a model input receiving an input signal, an error input, and a model output outputting a correction signal to said output transducer to introduce the canceling and shaping acoustic wave, a first summer, a second summer summing said correction signal from said first model and a desired signal and outputting the resultant sum to said output transducer, an auxiliary noise source introducing auxiliary noise such that said error transducer also senses the auxiliary noise from said auxiliary noise source, a second adaptive filter model having a model input from said auxiliary noise source and modeling said output transducer and the error path between said output transducer and said error transducer, a copy of said second adaptive filter model having an input from said desired signal, said first summer summing the output of said copy of said second model and the error signal from said error transducer and supplying the resultant sum to said error input of said first model, a third adaptive filter model having a model input from said auxiliary noise source and a model output summed at a third summer with said input signal, the result of the third summer is supplied to the model input.

19. The system according to claim 18 comprising a copy of said third adaptive filter model having an input from the output of said second summer and having an output, and a fourth summer summing said output of said copy of said third adaptive filter model and said output of said third summer and supplying the resultant sum to said model input of said first adaptive filter model.

20. The system according to claim 19 comprising a fifth summer having a first input from said output of said second summer and having a second input from said auxiliary noise source and supplying the resultant sum to said output transducer.

21. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, an adaptive filter model modeling said acoustic system and having a model input receiving an input signal, an error input, and a model output outputting a correction signal to said output transducer to introduce the canceling and shaping acoustic wave, a first summer summing the error signal from said error transducer and a desired signal and supplying the resultant sum to said error input of said model, a second summer summing said desired signal and said input signal and supplying the resultant sum to said model input.

22. The system according to claim 21 comprising an auxiliary noise source introducing auxiliary noise such that said error transducer also senses the auxiliary noise from said auxiliary noise source, a second adaptive filter model having a model input from said auxiliary noise source and a model output summed at a third summer with said input signal, a copy of said second adaptive filter model having an input from said correction signal and having an output summed with said input signal at a fourth summer having an output resultant sum supplied to said second summer for summing with said desired signal.

23. An active acoustic attenuation and spectral shaping system for attenuating and spectrally shaping an input acoustic wave comprising an output transducer introducing a canceling and shaping acoustic wave to attenuate and shape said input acoustic wave and yield an attenuated and spectrally shaped output acoustic wave, an error transducer sensing said output acoustic wave and providing an error signal, a first adaptive filter model modeling said acoustic system and having an error input and outputting a correction signal to said output transducer to introduce the canceling and shaping acoustic wave, a signal generator generating a desired signal, a first summer summing the error signal from said error transducer and said desired signal and supplying the resultant sum to said error input of said model, a second model modeling said output transducer and the error path between said output transducer and said error transducer, a copy of said second model having an input from said correction signal and having an output, a second summer summing the error signal from said error transducer and said output of said copy and outputting the resultant sum to said signal generator.

24. An active acoustic system for modifying an input acoustic wave to yield an output acoustic wave, comprising an error transducer sensing said output acoustic wave and providing an error signal, a first adaptive filter model having an error input responsive to said error signal and providing a correction signal, an output transducer responsive to said correction signal and introducing a modifying acoustic wave to combine with said input acoustic wave to generate said output acoustic wave, a second adaptive filter model modeling at least one of said output transducer and the error path between said output transducer and said error transducer, a signal generator responsive to said second adaptive filter model and to said error signal and generating a desired signal and combining said desired signal with said error signal provided to said error input of said first adaptive filter model.

25. An active acoustic system for modifying an input acoustic wave to yield an output acoustic wave, comprising an error transducer sensing said output acoustic wave and providing an error signal, an adaptive filter model having a model input responsive to an input signal and an error input responsive to said error signal and providing a correction signal, an output transducer responsive to said correction signal and introducing a modifying acoustic wave to combine with said input acoustic wave to generate said output acoustic wave, a signal generator generating a desired signal and combining said desired signal with said error signal at a first combiner and combining said desired signal with said correction signal at a second combiner, the result from the first combiner is supplied to the error input and the result from the second combiner is supplied to the output transducer, such that said desired signal is present in said output acoustic wave but absent from said error input to said adaptive filter model due to said combining of said desired signal and said error signal.

26. An active acoustic system for modifying an input acoustic wave to yield an output acoustic wave, comprising an error transducer sensing said output acoustic wave and providing an error signal, an adaptive filter model having a model input responsive to an input signal and an error input responsive to said error signal and providing a correction signal, an output transducer responsive to said correction signal and introducing a modifying acoustic wave to combine with said input acoustic wave to generate said output acoustic wave, a signal generator generating a desired signal and combining said desired signal with said error signal at a first combiner and combining said desired signal with said input signal at a second combiner, the result from the first combiner is supplied to the error input and the result from the second combiner is supplied to the model input, such that said desired signal is present in said output acoustic wave but absent from said error input to said adaptive filter model due to said combining of said desired signal and said error signal.

* * * * *